(12) United States Patent
Francis et al.

(10) Patent No.: US 8,899,418 B2
(45) Date of Patent: Dec. 2, 2014

(54) PACKAGING

(75) Inventors: David Francis, Roseville (AU); Scott Brackenreg, North Parramatta (AU)

(73) Assignee: McNeil-PPC, Inc., Skillman, NJ (US)

( * ) Notice: Subject to any disclaimer, the term of this patent is extended or adjusted under 35 U.S.C. 154(b) by 770 days.

(21) Appl. No.: 12/889,388

(22) Filed: Sep. 23, 2010

(65) Prior Publication Data
US 2012/0024735 A1 Feb. 2, 2012

(30) Foreign Application Priority Data
Jul. 29, 2010 (EP) .................................... 10251354

(51) Int. Cl.
| | | |
|---|---|---|
| A61L 15/00 | (2006.01) | |
| B65D 85/08 | (2006.01) | |
| A61F 13/551 | (2006.01) | |
| A61F 15/00 | (2006.01) | |
| B65D 5/32 | (2006.01) | |
| B65D 33/24 | (2006.01) | |
| B65D 83/02 | (2006.01) | |

(52) U.S. Cl.
CPC .......... *B65D 85/08* (2013.01); *A61F 13/55175* (2013.01); *A61F 15/003* (2013.01); *B65D 5/32* (2013.01); *B65D 33/243* (2013.01); *B65D 83/02* (2013.01)
USPC ....................................................... 206/440

(58) Field of Classification Search
USPC ........ 206/440, 438; 229/125.125, 203, 103.2, 229/117.28, 120.011, 125.08, 125.14, 229/125.37, 126, 160.1, 87.13, 12, 113, 229/115, 123.1, 123.2, 122, 222, 112, 116, 229/102, 115.222
See application file for complete search history.

(56) References Cited

U.S. PATENT DOCUMENTS

| | | | | |
|---|---|---|---|---|
| 385,924 | A | * | 7/1888 | Griswold ....................... 229/122 |
| 443,397 | A | * | 12/1890 | Mack ............................. 229/115 |
| 2,006,591 | A | * | 7/1935 | Fox .................................. 206/85 |
| 2,086,169 | A | | 7/1937 | Molins |
| 2,213,525 | A | | 9/1940 | LaFlamme |
| 2,277,097 | A | | 3/1942 | Hansen |
| 2,329,866 | A | * | 9/1943 | Van Sickels .................. 206/256 |
| 2,478,412 | A | | 8/1949 | McMahan |

(Continued)

FOREIGN PATENT DOCUMENTS

| | | |
|---|---|---|
| AU | 115150 | 9/1992 |
| AU | 117928 | 8/1993 |

(Continued)

*Primary Examiner* — Jacob K Ackun
*Assistant Examiner* — Jenine Pagan (57) ABSTRACT

A plurality of small packages, each for approximately a day's supply of tampons, are provided in an outer carrier box. The tampons in the small packages may be provided in a single row, and may be individually adhered to the bottom of the package. Each small package may be tapered to facilitate insertion of the individual package into a small space, such as a pocket, for discrete storage or carrying. The individual package may be formed with an inner box covered by an outer sleeve movable, like a flap, from the inner box to permit ready access to the contents of the inner box. A closure is provided that is resistant to inadvertent opening. The closure may be specifically configured for a tapered end of a tapered package. The closure may conceal the engaging elements thereof from view to inhibit inadvertent opening of the closure. If desired, a feedback feature, such as an auditory or tactile cue, may be provided by the closure to cue the user that the closure is securely closing the package.

1 Claim, 5 Drawing Sheets

(56) References Cited

U.S. PATENT DOCUMENTS

| | | | |
|---|---|---|---|
| 2,503,379 A | 4/1950 | Davis | |
| 2,867,320 A | 1/1956 | Andre | |
| 2,935,192 A * | 5/1960 | De Million-Czarnecki | 206/396 |
| 3,326,447 A | 6/1967 | Williamson | |
| 3,734,280 A | 5/1973 | Amneus et al. | |
| 3,823,864 A | 7/1974 | Ohkubo | |
| 4,043,097 A | 8/1977 | Ishida et al. | |
| 4,050,579 A | 9/1977 | Gorski et al. | |
| 4,194,624 A | 3/1980 | Spiegelberg | |
| 4,243,171 A * | 1/1981 | Prin | 229/117.16 |
| 4,286,639 A | 9/1981 | Murphy | |
| 4,570,797 A | 2/1986 | Weinman | |
| 4,648,513 A | 3/1987 | Newman | |
| 4,948,036 A * | 8/1990 | Loughman | 229/117.14 |
| 5,004,106 A | 4/1991 | Blumstock et al. | |
| 5,156,094 A | 10/1992 | Johansson et al. | |
| 5,180,059 A | 1/1993 | Shimatani et al. | |
| 5,531,325 A | 7/1996 | Deflander et al. | |
| 5,699,912 A | 12/1997 | Ishikawa et al. | |
| 5,797,494 A | 8/1998 | Balling et al. | |
| 5,827,251 A | 10/1998 | Moder et al. | |
| 5,884,771 A | 3/1999 | McCormick | |
| 5,891,127 A | 4/1999 | Moder et al. | |
| 5,964,741 A | 10/1999 | Moder et al. | |
| 5,986,165 A | 11/1999 | Moder et al. | |
| 6,010,001 A | 1/2000 | Osborn, III | |
| 6,024,219 A | 2/2000 | Froehlich et al. | |
| 6,045,544 A | 4/2000 | Hershberger et al. | |
| 6,131,736 A | 10/2000 | Farris et al. | |
| 6,164,442 A * | 12/2000 | Stravitz | 206/233 |
| 6,345,758 B2 | 2/2002 | Jaggi | |
| 6,478,763 B1 | 11/2002 | Simonsen et al. | |
| 6,523,690 B1 | 2/2003 | Buck et al. | |
| 6,585,131 B2 | 7/2003 | Huang et al. | |
| 6,592,004 B2 | 7/2003 | Huang et al. | |
| 6,604,651 B2 | 8/2003 | Amundson et al. | |
| 6,672,035 B1 | 1/2004 | Simonsen et al. | |
| 6,705,465 B2 | 3/2004 | Ling et al. | |
| 6,708,823 B2 | 3/2004 | Cottingham et al. | |
| 6,766,919 B2 | 7/2004 | Huang et al. | |
| 6,913,146 B2 | 7/2005 | Bechyne et al. | |
| 6,951,292 B2 | 10/2005 | Bando et al. | |
| 7,004,321 B1 | 2/2006 | Palm et al. | |
| 7,032,754 B2 | 4/2006 | Kopecky | |
| 7,073,684 B2 | 7/2006 | Decker et al. | |
| 7,144,391 B1 | 12/2006 | Kreutz et al. | |
| 7,159,717 B2 | 1/2007 | Aldridge et al. | |
| 7,178,671 B2 | 2/2007 | Nichols et al. | |
| 7,179,246 B2 | 2/2007 | Hansson | |
| 7,243,816 B2 | 7/2007 | Aochi | |
| 7,275,658 B2 | 10/2007 | Decker et al. | |
| 7,325,686 B2 | 2/2008 | Aldridge | |
| 7,422,106 B1 * | 9/2008 | Kendra | 206/440 |
| 2002/0056655 A1 | 5/2002 | Cottingham et al. | |
| 2002/0084203 A1 | 7/2002 | Cottingham et al. | |
| 2002/0096533 A1 | 7/2002 | Amundson et al. | |
| 2003/0023217 A1 | 1/2003 | McManus et al. | |
| 2003/0089633 A1 | 5/2003 | Sorebo et al. | |
| 2003/0102239 A1 | 6/2003 | Beard | |
| 2003/0116614 A1 | 6/2003 | Block et al. | |
| 2003/0222130 A1 | 12/2003 | Fukushima et al. | |
| 2004/0144679 A1 | 7/2004 | Sorebo et al. | |
| 2005/0011906 A1 | 1/2005 | Buck et al. | |
| 2005/0085780 A1 | 4/2005 | Corlett | |
| 2005/0085781 A1 | 4/2005 | Corlett | |
| 2005/0115855 A1 | 6/2005 | Hilel et al. | |
| 2005/0121349 A1 * | 6/2005 | Hodges et al. | 206/440 |
| 2005/0137553 A1 | 6/2005 | Bechyne et al. | |
| 2005/0252809 A1 | 11/2005 | Aldridge et al. | |
| 2005/0252817 A1 | 11/2005 | Aldridge et al. | |
| 2005/0255197 A1 | 11/2005 | Aldridge | |
| 2005/0255198 A1 | 11/2005 | Aldridge | |
| 2005/0255199 A1 | 11/2005 | Aldridge | |
| 2005/0269233 A1 | 12/2005 | Aldridge | |
| 2005/0284787 A1 | 12/2005 | Kopecky | |
| 2006/0071061 A1 * | 4/2006 | Velazquez et al. | 229/225 |
| 2006/0142720 A1 | 6/2006 | Zander et al. | |
| 2006/0151515 A1 | 7/2006 | Hood et al. | |
| 2006/0161125 A1 | 7/2006 | Bohlen et al. | |
| 2006/0212015 A1 | 9/2006 | Peele | |
| 2006/0266663 A1 | 11/2006 | Rhea | |
| 2007/0007158 A1 | 1/2007 | Cordes et al. | |
| 2007/0055213 A1 | 3/2007 | Erekson | |
| 2007/0090014 A1 | 4/2007 | Wheeler et al. | |
| 2007/0179466 A1 | 8/2007 | Tremblay et al. | |
| 2007/0199849 A1 | 8/2007 | Aldridge | |
| 2007/0209954 A1 | 9/2007 | Aldridge et al. | |
| 2007/0241124 A1 | 10/2007 | Buck et al. | |
| 2007/0246477 A1 | 10/2007 | Decker et al. | |
| 2008/0011627 A1 | 1/2008 | Tanbo | |

FOREIGN PATENT DOCUMENTS

| | | |
|---|---|---|
| AU | 150821 | 2/2003 |
| AU | 154594 | 2/2004 |
| AU | 2005229747 | 11/2005 |
| AU | 314080 | 5/2007 |
| CH | 443131 | 8/1967 |
| DE | 29602279 U | 3/1996 |
| DE | 19527393 | 2/1997 |
| DE | 29900827 | 4/1999 |
| EP | 0134227 | 5/1986 |
| EP | 1764067 | 3/2007 |
| FR | 1464879 | 3/1967 |
| FR | 365546 | 9/2006 |
| FR | 2887528 | 12/2006 |
| GB | 789627 | 1/1958 |
| GB | 2276611 | 5/1994 |
| JP | 2004017998 A | 2/2004 |
| WO | 8202530 | 8/1982 |
| WO | 0051897 | 9/2000 |
| WO | 0151378 | 7/2001 |
| WO | 03093119 | 4/2002 |
| WO | 0239943 | 5/2002 |
| WO | 03037744 | 5/2003 |
| WO | 2005110042 | 11/2005 |
| WO | 2005110864 | 11/2005 |
| WO | 2005110865 | 11/2005 |
| WO | 2005110876 | 11/2005 |
| WO | 2005110885 | 11/2005 |
| WO | 2005120989 | 12/2005 |
| WO | 2006003503 | 1/2006 |
| WO | 2006015688 | 2/2006 |
| WO | 2006028960 | 3/2006 |
| WO | 2006081855 | 8/2006 |
| WO | 2006094544 | 9/2006 |
| WO | 2007002481 | 3/2007 |
| WO | 2007052065 | 5/2007 |
| WO | 2007105182 | 9/2007 |
| WO | 2007140772 | 12/2007 |

* cited by examiner

PACKAGING

FIELD OF THE INVENTION

The present invention relates to packaging for articles such as tampons. More particularly, the present invention relates to a portable package for tampons which may be readily stowed and carried in a purse or pocket or in another discreet manner. The present invention additionally relates to a portable package permitting ready removal of the contents thereof, yet also permitting the package to be stowed readily in a small space. The present invention also relates to improvements to tapered packages. The present invention further relates to a closure for a package, such as, but not limited to, a tapered package.

BACKGROUND OF THE INVENTION

Packages for the storage and transportation of feminine hygiene articles for personal use are known. They have become increasingly popular as women are spending more time away from home and find it convenient to carry a small stock of their favorite personal hygiene articles with them. In particular, women like to carry a single day's supply of feminine hygiene articles in their purses, brief cases, satchels, and clothing pockets. Unfortunately, once a woman deposits the filled package in her purse, she often forgets about the package until a need arises. Often the package falls into the bottom of a purse and is exposed to dirt, loose coins, pens, and other miscellaneous paraphernalia. Sometimes the package is crushed, causing it to open on its own. This allows debris to enter into the package and/or the individual feminine hygiene articles to disengage from the package and to become unusable due to contamination or distortion. For this reason, such packages should be sturdy and discreet while also having the ability to keep the inner contents free from contamination. The package should also have a closure that ensures that the package remains closed and the feminine hygiene articles remain securely contained in the package during shifting of the various other contents within the purse.

Another issue related to carrying feminine hygiene packages within a purse or pocket can be noise. In some packages, especially digital tampon packages, once a tampon is removed, the remaining tampons have a certain degree of freedom to move or to rattle around within the package. This often results in noise being generated when the purse or clothing undergoes movement or shifting.

Many women, while maintaining their privacy as to their menstrual state, enjoy carrying accessories, such as purses, that are sleek and aesthetically pleasing. Some purses have open or zippered compartments on the sides. These compartments typically are pocket-like and are intended to be flat. It is not unusual for women to place loose or packages of feminine hygiene articles in these compartments. It is particularly desirable that the feminine hygiene articles do not bulge in the accessories in which they are contained so that they do not impair the overall image of such accessories. Having a small package that contains multiple feminine hygiene articles and that is suitable to be placed within the flat-like confines of a purse compartment requires that the package be designed such that the overall shape minimizes the package volume. Additionally, it is particularly beneficial to have a package that is shaped to facilitate insertion in a small space for stowage.

While discretion is important, the ability of the woman to retrieve the feminine hygiene article easily must not be compromised by the small size of the package. One way to achieve access to the inner contents of a package is to incorporate a reclosable lid or flap. Depending on the configuration of the lid, the resultant package may become bulky in size and shape. Bulky packages often result in bulges when carried in a pocket or a purse side compartment. Additionally, it is also important that the woman, whether in the privacy of a private or public bathroom, be able to remove, easily and without much manipulation of the package, a single feminine hygiene product such as a tampon without the fear of dropping the entire contents of the package.

Occasionally, the individual or packaged articles fall out from the purse when the woman tries to retrieve objects from the purse or compartment, resulting in embarrassing situations, especially among mixed company. Therefore, it would be desirable to have a discreet package that also assures that the individual feminine hygiene articles do not inadvertently fall out.

Various closures for small packages are known in the art to permit ready opening to access the contents of the package, and also to permit reclosing of the package. Because a small package may be placed in a tight space, it is particularly desirable to provide a closure that resists inadvertent opening upon removal of the package from the tight space. This is particularly the case with packages for feminine hygiene articles, to prevent the contents from falling out upon removal of the package.

SUMMARY OF THE INVENTION

There is therefore a need for a package for storing feminine hygiene articles that holds tampons securely in place while maintaining them in a clean environment. In accordance with the principles of the present invention, a single day's supply of feminine hygiene articles is provided in a ready-made package of tampons containing and ready for a woman to carry with her in a discreet manner throughout her day out of her house. A plurality of such packages preferably is provided in an outer retail pack in which multiple such day packs are contained. The purchaser simply needs to remove one of the ready-made day packs for a day's use, without any need to remove a given number of tampons for the day and to place them in a separate container. Thus, in accordance with one aspect of the present invention, a day's supply of tampons is provided in a small pack that has been pre-packaged for ready removal from a master carton and stowage for use when needed.

In accordance with another aspect of the present invention, tampons are provided in a package slim enough to be stowed in a tight or narrow space, such as a small purse or in a pocket. For instance, tampons may be arranged in a single row in a disposable package. The tampons may be removed along their longitudinal axes. The resulting package may be readily stowed in a small space and the tampons may be removed without the need for a lot of space to open the package (as is the case with existing clamshell type cases for tampons). The tampons may be adhered to the base of the package. It will be appreciated that the arrangement of tampons in a single row in a package, formation of a package so that tampons are removed along their longitudinal axes, and/or adherence of tampons to the base of the package in which they are contained are all features that are beneficial to a day pack formed in accordance with the principles of the present invention, but which may also be beneficial in other tampon packages.

In accordance with a related aspect of the present invention, the outer contour of the tampon package may be configured to be slim with a tapered end. As such, the package may be readily inserted into a small space so that the package may be carried discreetly. Such tapering can be achieved in any of a variety of manners. For instance, the top ends of opposite walls of the package can be directly coupled together to result in the desired tapering of the package. Moreover, the closure of the package should be easy to open when desired, but sturdy enough or otherwise formed so that it is resistant to opening upon insertion into its stowage location, during stowage, or upon removal from its stowage location. It is also helpful to the user if a cue is given once the package is securely closed. This cue may be a slight clicking noise or a tactile sensation that the user's fingers detect.

Individual day packs formed in accordance with the principles of the present invention may have further beneficial characteristics that may be applied to packagings other than such day packs and packagings for items other than tampons. For instance, to facilitate removal of a tampon along its longitudinal axis, a day pack may be formed with an inner box in which the tampons are arranged, and with an outer sleeve forming a front flap and a back flap covering the inner box and the tampons therein. Either or both flaps may be moved away to reveal the inner box and to permit removal of a tampon from an end of the inner box in a direction along the longitudinal axis of the tampon. Such package has benefits independent of its usage for packaging tampons. For instance, a package formed with an inner box and outer sleeve in accordance with the principles of the present invention permits such package to be tapered to fit into a small space. The flaps formed by the outer sleeve may be directly coupled together to achieve the desired tapered configuration.

In accordance with yet another aspect of the present invention, a closure is provided with various unique features. For instance, a closure formed in accordance with the principles of the present invention may be formed such that it may be used on a tapered package. If a package is tapered, the closure often is even more susceptible to inadvertent opening upon removal of the package, or even mere manipulation of the package in its storage location. Such closure may have various beneficial features that may be applied to packages other than tapered ones. One such feature is the provision of a covering element that covers the engaging elements of the closure. Thus, even if the package is stowed in a tight space, removal of the package should not disengage the engaging elements of its closure because a covering element covers and protects the engaging elements from inadvertent opening. Another feature of the closure that is particularly beneficial when provided in conjunction with a closure with a covering element (though beneficial without such covering element) is a closure that provides feedback, such as a cue, to the user when engaged and closed. The feedback may be a tactile and/or auditory cue generated upon engaging the engaging elements of the closure to close the package.

These and other features and advantages of the present invention will be readily apparent from the following detailed description of the invention, the scope of the invention being set out in the appended claims.

BRIEF DESCRIPTION OF THE DRAWINGS

The detailed description will be better understood in conjunction with the accompanying drawings, wherein like reference characters represent like elements, as follows.

DETAILED DESCRIPTION OF THE INVENTION

In accordance with the principles of the present invention, a package is formed for convenient and ready portability as well as ease of use. It will be appreciated that separate and independent aspects of the present invention are described herein. Such aspects, at least alone, have unique benefits, and, although may enhance one another, need not be provided in conjunction with one another. In other words, each aspect of the present invention has unique individual benefits and thus may be provided without any, or with only one, or with some but not all, or with all of the other aspects disclosed herein.

Figure 1:
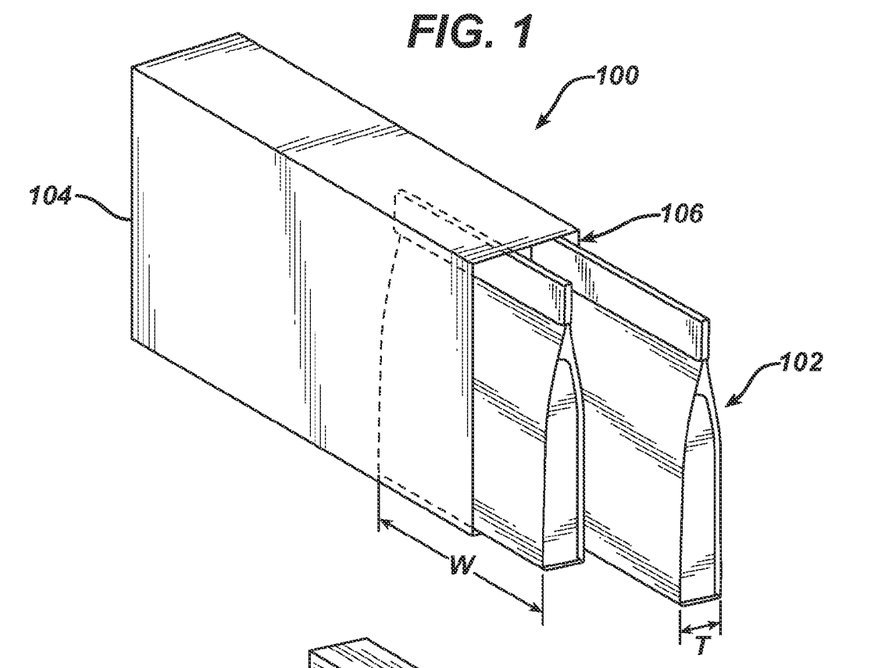
FIG. 1 is a perspective view of an exemplary retail pack of individual packages each containing a day's supply of tampons in accordance with the principles of the present invention.

Referring to FIG. 1 of the drawings, a retail package of tampons 100 formed in accordance with one aspect of the present invention is sold containing a plurality of smaller packages 102. Each of the smaller packages 102 is sized to contain a limited number of tampons and thus is more portable than the entire retail package. The number of tampons contained within smaller package 102 may be selected to satisfy any of a variety of an individual's needs for carrying tampons. One common need for a small package of tampons is a desire to carry a number of tampons outside the home, sufficient for a day's use such that the entire retail package (containing several days' supply) need not be taken along. In accordance with the principles of the present invention, smaller package 102 may be sized and shaped to carry a day's supply and thus is conveniently referenced herein as a "day pack" 102. Preferably, day pack 102 is sized, shaped, and configured to be carried readily in a purse or pocket. It will be appreciated that although the principles of the present invention are described in conjunction with packaging for tampons, such principles may be applied to packages for other articles.

The number of tampons to be contained within day pack 102 preferably is preferably selected based on one or more of the following factors: the need of a typical user in a typical time frame in which a typical user is away from home (such as 12-18 hours), the ultimate desired size of day pack 102, the absorbency level of the tampons (higher absorbency tampons typically having a larger thickness or diameter and thus taking up more space than lower absorbency tampons). For instance, day pack 102 may be sized to hold no more than four or five tampons, and preferably no more than four tampons. Such size not only accommodates the typical user's needs for a day, but also permits ready and discreet stowage of day pack 102 in a purse or even in a pants pocket.

Although carrying cases for tampons (such as for a day's supply of tampons) have been known in the art, day pack 102 is unique in that only a day's supply of tampons is prepackaged and sold in day pack 102. Thus, there is no need to locate a carrying case, remove the desired number of tampons, and place them in the carrying case, because day pack 102 already is pre-packaged and sold to contain the typical number of tampons needed by a user during the day while away from home. A plurality of day packs 102 may be provided in a single master box or outer box or retail box or carrier or retail pack 104 (all such terms referring to the box the consumer sees on the retail display space, such as a shelf, and which has sealed therein the complete number of tampons for retail purchase; such box hereinafter referenced as "retail pack" for the sake of simplicity without intent to limit). As such, instead of simply providing a given number of tampons in the outer retail packaging, retail pack 104 provides several individual day packs 102, each prepackaged for a single day, for convenience. Thus, a user simply needs to take a day pack 102 from retail pack 104 to have sufficient tampons for the day, without the need to remove tampons from the retail box and transfer such tampons to a separate carrying case. Preferably, day pack 102 is formed to be disposable for complete user convenience. More preferably, day pack 102 is formed of a thin material to reduce its size, as well as to reduce waste (upon disposal once the tampons therein have all been used). Most preferably, the material is biodegradable.

If desired, retail pack 104 may have at least one open side 106 so that the day packs 102 therein may be viewed. A user may thus readily see the unique packaging of tampons within retail pack 104. Moreover, if day pack 102 has a unique shape (such as a tapered shape, as embodied in day pack 102 of FIGS. 3 and 4 described in further detail below), such unique shape may be readily viewed through open side 106.

Because it is typically desirable for a portable package or holder or case for tampons to be discreet, and capable of being stowed in a small space (such as in a purse, a compartment of a purse or other larger item, or a pocket), it may be desirable for day pack 102 to be as slim as possible. For instance, tampons 110 to be held in day pack 102 may be aligned in a single row with their longitudinal axes A parallel to one another and substantially perpendicular to the bottom wall or base 120 of day pack 102. Such arrangement minimizes the thickness T of day pack 102, as may appreciated with reference to the exemplary open day pack 102 illustrated in FIG. 2. Thus, according to one aspect of the present invention, a day pack 102 for tampons is sized and configured to contain only a single row of no more than four or five, and preferably four, tampons 110.

Figure 2:
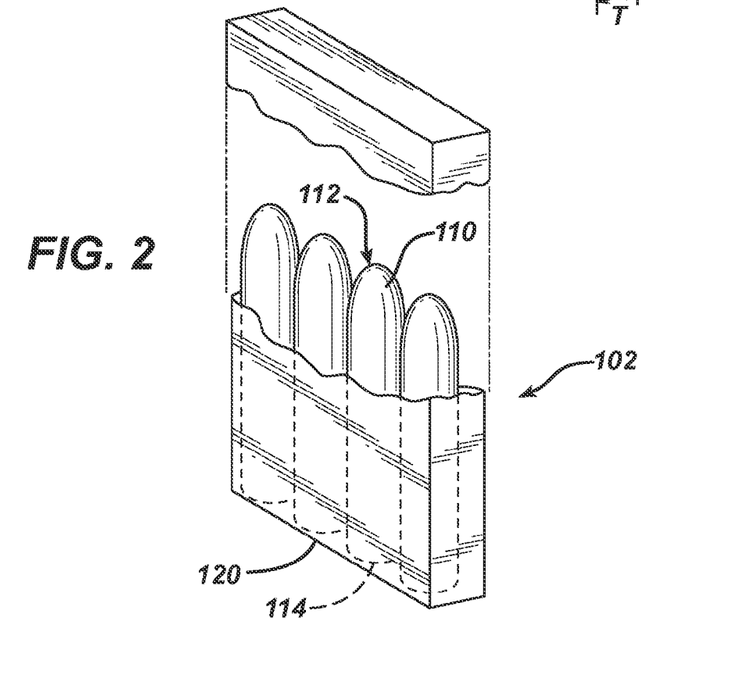
FIG. 2 is a partially cutaway perspective view of a package containing a day's supply of tampons in accordance with the principles of the present invention.

Provision of tampons in only a single row in a disposable package such as day pack 102 may provide the further benefit of reducing the possibility or likelihood that the tampons will be crushed as tampons are removed from day pack 102. This is so because if thickness T of day pack 102 is great enough for only a single tampon, then the tampons within day pack 102 may shift laterally along width W of day pack 102, but cannot bunch along thickness T. Thus, with only one degree of motion, shifting of the tampons in day pack 102 is reduced and the tampons have a reduced likelihood of becoming crushed against one another than if the tampons could shift in further directions against one another. This aspect of the invention is particularly beneficial if the tampons within day pack 102 are the digital type and thus do not benefit from the protection against crushing afforded by an applicator.

In accordance with yet a further aspect of the present invention, tampons may be maintained in their positions within day pack 102 through the use of a light adhesive or wax. Since, as illustrated in the exemplary embodiment of FIG. 2, tampons that are digitally inserted may have a somewhat domed, curved or otherwise bullet-shaped leading insertion end 112, it is preferable to utilize adhesive along the flatter withdrawal end 114 to adhere such end to the base 120 of day pack 102. Any known material used for releasably securing and/or adhering a light-weight, wrapped article to a packaging material (such as cardboard or paperboard) may be used. For example, wax or glue dots may be used, as these types of adhesives do not form permanent bonds between the wrapper material surrounding the tampon (e.g., such as the wrapper materials disclosed in WO 2004/080362, published Sep. 23, 2004, and incorporated by reference herein in its entirety) and most materials commonly used to form the package. The adhesive preferably is selected to have any or all of the following properties: does not dry out readily, holds the tampons securely, permits ready removal of the tampons when intentionally pulled from day pack 102. Such adhesive may be useful in keeping the tampons in place to reduce shifting further, thereby further reducing the likelihood of tampons remaining in day pack 102 from being crushed as tampons are removed from day pack 102. Reduction of shifting of tampons 110 within day pack 102 is also desirable to reduce any noise (such as rattling) that may be generated as tampons shift within day pack 102 and against one another and the interior of day pack 102. Moreover, such adhesive may be beneficial in maintaining tampons within day pack 102 so they do not unintentionally fall out of day pack 102. Preferably, the degree of adhesion is sufficient to maintain tampons 110 within day pack 102 in a substantially upright position (so the tampons 110 do not tilt or lean against one another if one or more have been removed from day pack 102 already), yet to permit ready intentional removal of a tampon 110, such as by twisting and pulling the tampon. A tampon 110 thus may be removed along its longitudinal axis A.

The slim configuration of day pack 102 is further enhanced when a relatively thin material is used to form day pack 102. Preferably, the material is selected so that it does not significantly contribute to thickness T of day pack 102 and thickness T is not much greater than the thickness of the tampons within day pack 102. Additionally, the material preferably also is sturdy enough to protect the tampons within day pack 102 from damage, deformation, moisture, and contamination, etc., yet lightweight enough not to affect significantly the weight, bulk, portability, etc. of day pack 102. Preferably, the material is readily crushable once emptied of its contents and preferably biodegradable and/or readily recyclable. An exemplary material from which day pack 102 may be formed is paperboard. The paperboard may be selected to deform more readily than cardboard to facilitate use of day pack 102. Paperboard having a thickness of approximately 0.35 mm has been found to be satisfactory and to achieve the desired sturdiness without adding significantly to the thickness of day pack 102.

Day pack 102 may be formed of a material that imparts day pack 102 with a clearly defined shape that is maintained independently of the contents of day pack 102, and thus maintains the original configuration of day pack 102. However, it will be appreciated that more flexible paperboard, or other more flexible materials that conform to the shape of the contents of the pack may be used instead without detracting from the features of the present invention (such as the provision of only one day's supply in a package). For instance, a plastic material may be used that also imparts water impermeability. Such plastic may be a flexible liquid impermeable material currently known in the art for forming pouches or sanitary absorbent article overwrap, thus forming a soft-sided package. For example, the material is preferably made from a thin plastic film or a nonwoven film which is made liquid-impermeable through coating or treatment with a liquid-resistant material. It will be appreciated that the use of a thin material is beneficial for the formation of a small package of tampons containing a day's supply, regardless of whether the package contains a single row or another configuration of tampons therein. The material selected may permit further beneficial features in accordance with the principles of the present invention described below.

If paperboard is used to form day pack 102, such paperboard may be formed or selected to be resistant to moisture. For instance, a coated paperboard, such as those available and known to those of ordinary skill in the art, may be used. One example of a coating material is celloglaze, a general term used for biaxially-oriented polypropylene films, which are one type of thin plastic films. Other manners of achieving moisture protection could be coating the paperboard with varnish via a printing process. A single material is preferred but not critical to the invention.

As may be appreciated from the above descriptions of different independent aspects of the present invention, such as the size of the day pack to hold not more than four or five (more preferably four) tampons, the slim shape of the day pack, and the use of a thin material for forming the day pack, a desirable characteristic of a day pack formed in accordance with principles of the present invention is the provision of a tampon package that may readily be inserted into a small space, such as a pocket or a small purse or a small compartment in another article (such as a compartment of a purse). In accordance with another independent aspect of the present invention, a day pack may have at least one side or end or edge (referenced herein as an "end" for the sake of convenience and without intent to limit) that is tapered. Such tapering provides various independent benefits, such as facilitating insertion of the day pack into a pocket or otherwise tight space and distinguishing one end from the others so a user may determine the orientation of the day pack tactilely and without the need to look at the day pack or even pull out the day pack from her purse. As illustrated with reference to FIG. 3, at least one end of exemplary day pack 202, such as top end 204, may be narrower than the other ends, such as by tapering such end. Such tapering facilitates insertion of day pack 202 into a tight space with tapered top end 204 as a leading insertion end. The tapering permits initial insertion of day pack 202 into the tight space and gradual widening of the tight space to receive the full thickness T of day pack 202 and thus the thickness of the tampons within day pack 202. It will be appreciated that the taper may be selected to follow the typical domed, curved, or otherwise bullet-shape of the top of a tampon (particularly a digital tampon), such as exemplary tampon 210 shown in FIG. 4 (which Figure illustrates day pack 202 in an open configuration). Such tapering provides the added benefit of reducing material used to form day pack 202 (by following the shape of the contents of day pack 202, less material is used to form day pack 202 than used for a squared-off or flat top). Moreover, such tapering further reduces the possibility of crushing the contents of day pack 202 and day pack 202 itself because of the reduction of empty space between day pack 202 and the tampons therein.

Figure 4:
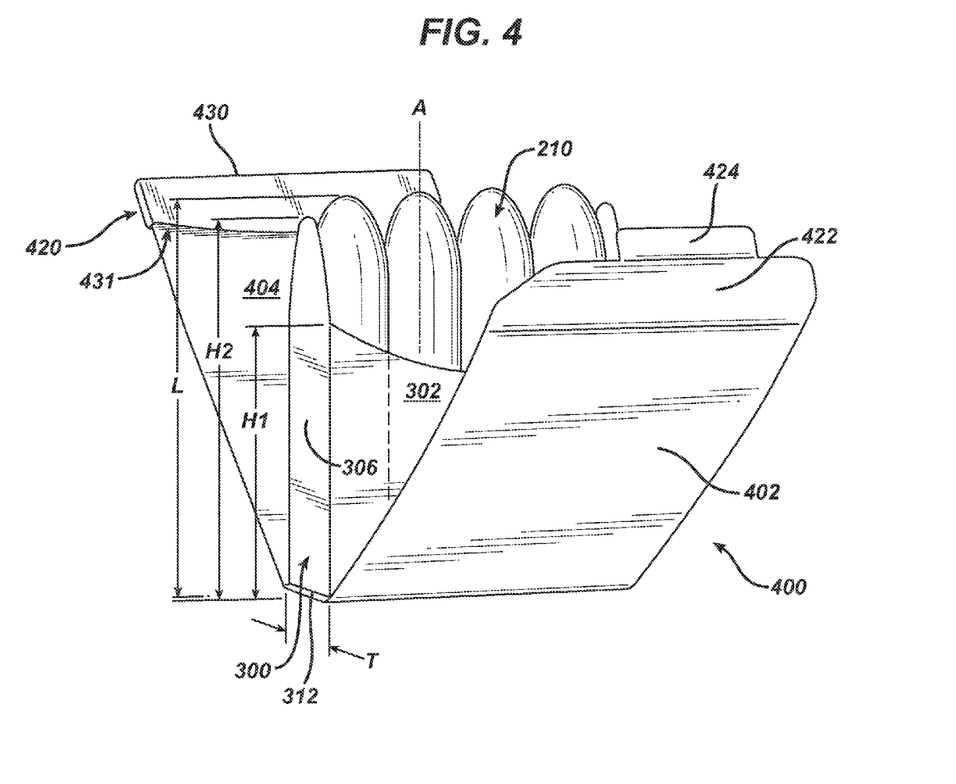
FIG. 4 is a perspective view of the package of FIG. 3 in an open configuration.
Figure 5:
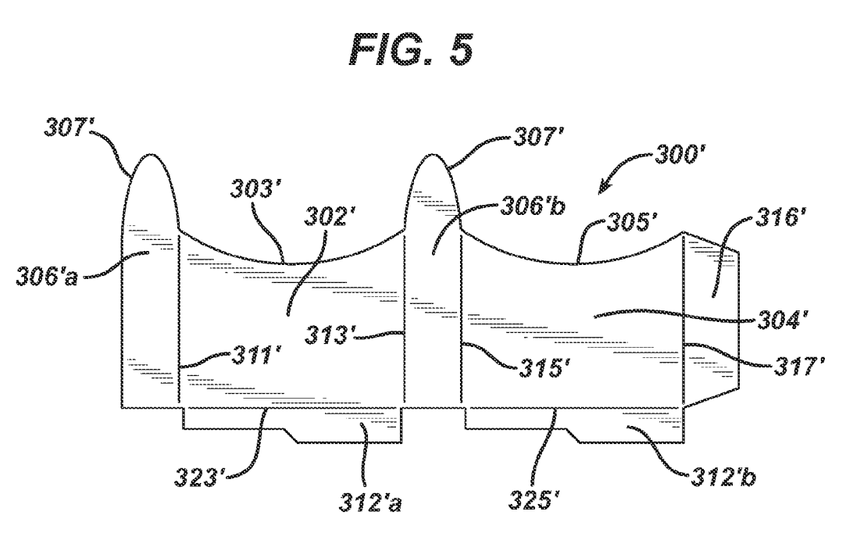
FIG. 5 is a plan view of an exemplary blank that may be used to form the inner box illustrated in FIG. 4.
Figure 6:
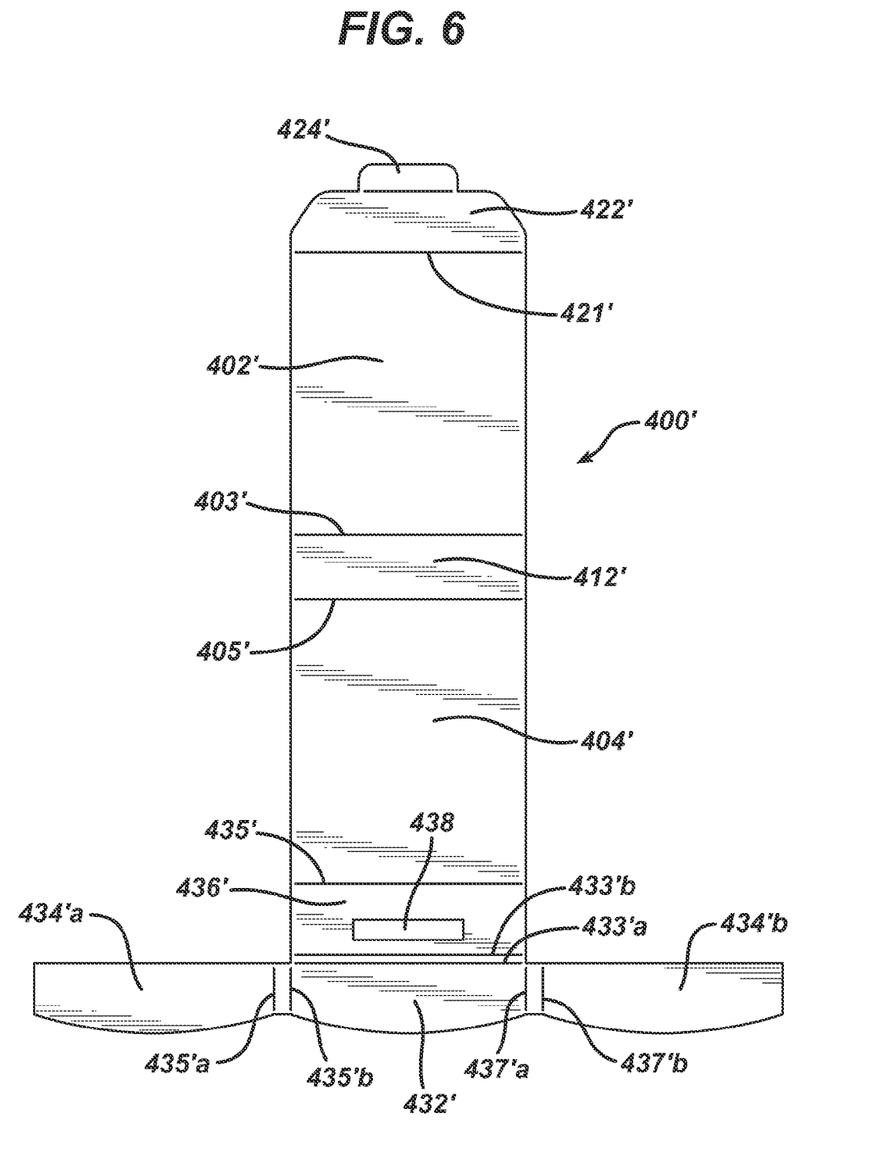
FIG. 6 is a plan view of an exemplary blank that may be used to form the outer sleeve illustrated in FIG. 5.

One manner of forming a day pack 202 to have a tapered end 204 yet to permit ready and easy access to the contents therein is illustrated in FIG. 4. Exemplary day pack 202 of FIG. 4 is formed with an inner box 300 and an outer sleeve 400, exemplary blanks for which are illustrated in FIGS. 5 and 6, respectively, and will be described in further detail below. It is noted that directional references such "top," "bottom," "front," "back", and "side" do not limit the respective walls or panels to such orientation, but merely serve to distinguish these walls or panels in FIGS. 3-6 from one another. It will be appreciated that the benefits of an inner box and outer sleeve arrangement are independent of the potential of tapering the package resulting from an inner box and outer sleeve arrangement, as will become apparent. Accordingly, the concept of tapering need not be applied to packaging utilizing an inner box 300 and outer sleeve 400.

Referring to FIG. 4, exemplary inner box 300 is formed to have at least one wall that extends only partially along the length L of a tampon 210 to be contained therein. As may further be appreciated with reference to both FIGS. 4 and 5, it is particularly convenient (though not essential) to provide two walls, such as front wall 302 and back wall 304 (hidden from view by tampon 210), with maximum heights H1 shorter than length L of tampon 210. The provision of at least one wall of inner box 300 with a height shorter than the length L of tampon 210 therein permits ready grasping of tampon 210 for easy removal from inner box 300. Side walls 306 of inner box 300 need not be shorter than tampons 210. In the embodiment of FIG. 4, side walls 306 may have a height H2 extending at least or almost the entire length of tampon 210. If desired, side walls 306 may be shaped to follow the cross-sectional shape of tampons 210 such that when day pack 202 is closed (as in FIG. 3), tampons 210 are substantially completely covered by side walls 306, thereby protecting tampons 210 from damage or contamination, and also hiding tampons 210 from view.

Because the top portions of tampons 210 are exposed above at least one wall of inner box 300 in the embodiment of FIG. 4, the walls of inner box 300 need not be manipulated or otherwise altered in order to remove a tampon (as would be the case if the tampons were completely enclosed by the side walls of inner box 300, in which case a user would have to insert her fingers within inner box 300 and between a tampon and the inner surface of at least two of the side walls or between tampons or between a wall and a tampon to grasp and to remove a tampon). Thus, inner box 300 may be sized and dimensioned to follow closely and to conform to the row of tampons 210 to be contained therein, thereby reducing the material required to form inner box 300 and reducing the likelihood of shifting of tampons 210 therein (because almost no extra space is provided). Tampons 210 may be securely held within day pack 202 by virtue of a tight tolerance with inner box 300, and tampons 210 thereby may be inhibited if not prevented from falling out of inner box 300 unintentionally. Thus, although formation of a package with an inner box 300 covered by an outer sleeve 400 facilitates formation of a tapered end of the package, such arrangement also permits reduced deformation of the package upon removal of tampons 210 as well as reduction of packaging materials regardless of whether the package has a tapered end.

An exemplary blank 300' for forming inner box 300 of FIG. 4 is illustrated in FIG. 5. Front panel 302' and back panel 304', respectively forming front wall 302 and back wall 304 of inner box 300 of FIG. 4, are shorter than side panels 306'*a* and 306'*b*. Respective top edges 303' and 305' of front wall 302' and back wall 304' are arcuate, but may be any other shape instead, including straight. Side panels 306'*a* and 306'*b* have arched upper edges 307' to follow the shape of a tampon 210 to be contained within the inner box 300 to be formed from blank 300'. However, upper edges 307' may be shaped in any other desired manner, including squared off (such as if day pack 202 is not formed with a tapered end 204). To form the enclosing walls of inner box 300 (the walls enclosing tampons 210 with respect to which tampon longitudinal axes A are preferably held substantially parallel), panels 306'*a*, 302', 306'*b*, and 304' of blank 300' are folded along respective fold lines 311', 313', and 315', and side connecting panel 316' is folded along fold line 317' and coupled to the inner-facing (tampon-facing) surface of side panel 306'*a*. In addition, bottom panels 312'*a* and 312'*b* are folded along fold lines 323' and 325', respectively, and are laid over each other (the specific arrangement of which panel is above the other is not critical) to form a bottom wall 312 of inner box 300.

As may be appreciated, it is desirable to protect tampons 210 to be contained within inner box 300 of exemplary day pack 202 from damage, deformation, moisture, contamination, etc. As noted above, by having inner box 300 reflect the shape of tampon 210 to be contained therein, tampons 210 are held securely in place and thereby are protected from being compressed against one another. Additionally, the inner box shape can protect the contained tampons 210 from coming into contact with dirt, dust, debris, and other contaminants as the edges of inner box 300, front panel 402, and back panel 404 closely abut and leave little room for contaminants to enter. In the exemplary embodiments of FIGS. 4 and 5, outer sleeve 400 covers the portion of tampons 210 exposed above the shorter front wall 302 (and, optionally shorter back wall 304) of inner box 300. If, as in the exemplary embodiment of FIGS. 4 and 5, side walls 306 extend substantially the full height of tampons 210, then outer sleeve 400 together with side walls 306 enclose and protect tampons 210 within inner box 300.

In accordance with one aspect of the present invention at least front wall 402, and optionally back wall 404 as well, of outer sleeve 400 may function as a flap that selectively covers the exposed portions of tampons 210 and may be moved away from inner box 300 to permit ready and easy removal of a tampon 210 from inner box 300. Such flap may be sized, dimensioned, and otherwise configured to facilitate one-handed manipulation so a user may open day pack 202, remove a tampon therefrom, and close day pack 202 with one hand, and even while day pack 202 remains in the user's purse or pocket (or other stowage location). Formation of front wall 402 and back wall 404 as flaps also facilitates the formation of the above-noted tapered end 204. However, a standard squared off top end, optionally with a hinged lid or other type of access to inner box 300, may be provided instead, if desired.

An exemplary blank 400' for forming outer sleeve 400 of FIG. 4 is illustrated in FIG. 6. For the sake of convenience, which will become apparent with respect to further descriptions of outer sleeve blank 400' below, outer sleeve blank 400' will be described with reference to FIG. 6 as having its outer surface shown (the inner surface, which faces inner box 300 in FIG. 4, being on the other side of outer sleeve blank 400' not visible in FIG. 6). Front panel 402' is folded along front fold line 403' with respect to bottom panel 412' and back panel 404' is folded along back fold line 405' with respect to bottom panel 412' (both front panel 402' and back panel 404' being folded in a direction into the page bearing FIG. 6) to form front wall 402 and back wall 404 of outer sleeve 400, as illustrated in FIG. 4. Bottom wall 312 of inner box 300 preferably is coupled to the inner surface of bottom panel 412' to situate outer sleeve 400 properly over inner box 300 to cover and to close over tampons 210 within inner box 300. If desired, outer sleeve 400 may be secured over and to inner box 300, such as by adhesive.

Outer sleeve 400 may be formed in any desired manner to contribute to the external appearance of day pack 202. In accordance with one aspect of the invention noted above, the formation of day pack 202 from an inner box 300 and an outer sleeve 400 permits day pack 202 to be readily formed with at least one tapered end 204 to facilitate insertion of day pack 202 into a confined space. An exemplary embodiment of a tapered day pack 202 with a tapered end 204 is illustrated FIGS. 3, 4, and 6. Nonetheless, it will be appreciated that the formation of day pack 202 from an inner box 300 and an outer sleeve 400 provides independent benefits such that a day pack so formed need not have a tapered end to provide unique benefits. For instance, formation of day pack 202 from an inner box 300 and an outer sleeve 400 provides the ability to form as small a package as possible with relatively sturdy yet flexible material, and the ability for the tampons to extend above a portion of the packaging so a tampon may be removed without deforming the packaging.

Figure 3:
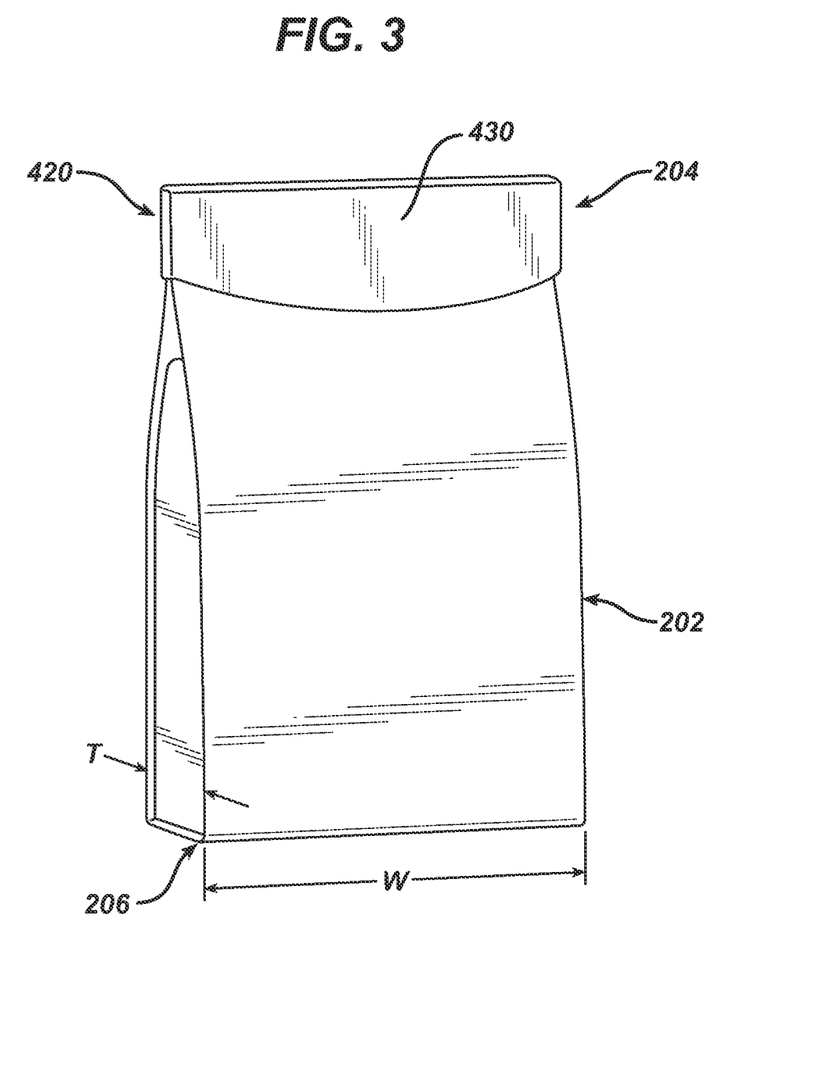
FIG. 3 is a perspective view of an exemplary tapered package in accordance with the principles of the present invention.

It is generally desirable to maintain a day pack formed in accordance with the principles of the present invention in a closed configuration to cover and to protect the tampons held therein, as well as to prevent the tampons from falling out. The exemplary day pack 202 of FIGS. 3 and 4 is provided with a closure 420 that includes a cover element that covers and protects the actual engaging elements of the closure so that the engaging elements cannot be inadvertently disengaged from one another, such as upon stowage of day pack 202 or removal of day pack 202 from stowage or simply while day pack 202 is in its stowed location. Exemplary closure 420 of FIGS. 3 and 4 has a cover element resembling a band encircling and holding together the top ends of front wall 402 and back wall 404 of outer sleeve 400 (such as flat against each other) and covering the closure elements. However, it will be appreciated that other closures for a tapered end of a package may be used instead, whether or not resembling a band, holding walls 402 and 404 flat against each other, or otherwise. It is further noted that although closure 420 is formed and provided in a manner that permits outer sleeve 400 to maintain the taper at tapered end 204, various of the benefits provided by closure 420 are independent of closure 420 permitting and/or maintaining the taper of a tapered package, as will be appreciated with reference to the following more detailed description of exemplary closure 420.

The exemplary outer sleeve blank 400' of FIG. 6 illustrates panels that may be used to form closure 420 with several unique features and benefits. As described above, outer sleeve blank panels 402', 412' and 404' are folded to form an outer sleeve 400 as in FIGS. 4 and 5. As such, closure flap 422, formed from closure flap panel 422', is oriented at the top end of front wall 402 with a closure tab 424, formed from closure tab panel 424', extending therefrom (in the case of the exemplary embodiment of FIG. 6, from a free edge of closure flap panel 422'). Covering closure panel 432' is folded towards the inner surface (on the other side of the surface shown in FIG. 6) of outer sleeve blank 400' and with respect to closure panel 436' along fold lines 433'a and 433'b to cover closure slot 438 within closure panel 436' at the top end of back wall 404, for reasons that will become apparent. The provision of two fold lines 433'a and 433'b allows covering closure panel 432' to be spaced sufficiently from closure panel 436' to form a receiving channel 431 therebetween (see FIG. 4) that is wide enough to receive closure flap 422 and closure tab 424. After covering closure panel 432' has been folded with respect to closure panel 436', side closure panel 434'a is folded with respect to covering closure panel 432' along fold lines 435'a and 435'b towards the outer surface of back panel 404'. Similarly, side closure panel 434'b is folded with respect to covering closure panel 432' along fold lines 437'a and 437'b and towards the outer surface of back panel 404'. Once again, the provision of a pair of fold lines 435'a and 435'b and 437'a and 437'b allows covering closure panel 432' to be spaced from closure panel 436' to form receiving channel 431 therebetween. Side closure panels 434'a and 434'b are laid over each other (the order being immaterial) to secure closure panels 432', 434'a, and 434'b in place to form a closure band 430 encircling closure slot 438. As will be appreciated, to close exemplary day pack 202, closure flap 422 is inserted into receiving channel 431 within closure band 430, and closure tab 424 is inserted into closure slot 438. Closure flap panel 422' is slightly folded along fold line 421' with respect to front panel 402' and closure panel 436' is slightly folded along fold line 435' so that closure flap panel 422' and closure panel 436' are laid substantially flat against each other, thereby maintaining the taper of tapered end 204 of day pack 202. Moreover, the folding of side closure panels 434'a and 434'b over each other and over the outer surface of closure panel 436', and the folding of covering closure panel 432' over the inner surface of closure panel 436' results in a multi-layered region at the tapered section 204 of day pack 202. Such multiple layers add strength to tapered section 204, which otherwise would be far more flexible and potentially subject to bending and possible damage, particularly in an embodiment in which tapered section 204 extends above the tampons 210 (or other articles to be contained in a package such as day pack 202) and thus is not strengthened or reinforced by the material of tampons 210.

There are several manners in which closure 420 may serve to inhibit unintended opening of day pack 202. As indicated above, receiving channel 431 is sized to permit insertion of closure flap 422 and closure tab 424 therein. The size of receiving channel 431 may be selected to maintain closure flap 422 securely therein. For instance, closure flap 422 and closure tab 424 may be slid into receiving channel 431 along closure panel 436' (given the narrowness of receiving channel 431) to insert closure tab 424 into closure slot 438. If desired, receiving channel 431 may be sized to maintain closure flap 422 in close contact with closure panel 436'. Closure side panels 434'a and 434'b, once folded to cover the outer surface of closure panel 436', serve as a retaining panel to retain closure tab 424 in closure slot 438, such as by preventing closure tab 424 from being caught on another object and dislodged from slot 438. Alternatively or additionally, receiving channel 431 may be sized to cause closure tab 424 to fold towards the inner surface of closure flap 422 upon insertion into receiving channel 431. As such, closure tab 424 takes on a configuration reminiscent of a fish hook or barb so that closure tab 424 can be hooked readily into closure slot 438. Closure band 430 may be configured to hold closure flap 422 in place within receiving channel 431 so that closure tab 424 likewise remains in place within closure slot 438 and does not inadvertently come out of closure slot 438. If desired, side closure panels 434'a and 434'b may be formed and folded with respect to closure panel 436' to maintain closure tab 424 hooked within closure slot 438. For instance, side closure panels 434'a and 434'b may help to catch closure tab 424 in closure slot 438 by holding closure tab 424 in the folded over position, hooked into closure slot 438. Also, side closure panels 434'a and 434'b cover the outer surface of closure slot 438 from which closure tab 424 extends so that closure tab 424 cannot catch on anything and inadvertently be unhooked and dislodged from closure slot 438.

An additional feature that closure 420 may provide is a cue or feedback feature that confirms that closure 420 is securely closed. Such feedback is particularly desirable if the engaging elements of closure 420 are hidden by a cover element such as closure band 430. In particular, the arrangement of side closure panels 434'a and 434'b with respect to closure panel 436' and closure slot 438 permits closure tab 424 to be held in close contact with side closure panels 434'a and 434'b and closure panel 436' upon insertion of closure tab 424 into closure slot 438. Such close contact not only helps to keep closure tab 424 in place within closure slot 438, but may also provide feedback to the user confirming secure closing of closure 420. Such feedback may be tactile, as a result of the close fit of closure tab 424 within closure slot 438 and between side closure band panels 434'a and 434'b and closure panel 436'. Preferably, the feedback is audible as well, such as a small click confirming closure tab 424 is securely held in place within closure slot 438. In an embodiment in which closure flap 422 and closure tab 424 are slid into receiving channel 431, the feedback indicates when closure flap 422 and closure tab 424 have been slid sufficiently with respect to closure panel 436'.

The provision of a feedback cue to the user that day pack 202 has been properly closed is considered to be a desirable feature for tampon packaging. In particular, in accordance with the principles of the present invention, such feedback is provided on a disposable packaging for carrying a day's supply of tampons. Thus, a relatively inexpensive package for only a day's supply of tampons provides the user with feedback confirming such package has been properly closed so that the user is assured the contents will not inadvertently spill out.

It will be appreciated that although the above-described closure 420 is described as being formed in a paperboard package, other materials may be used. Moreover, the above-described closure 420 has several beneficial features, including, without limitation, easy opening, resistance to inadvertent opening, sturdiness, feedback to confirm proper closure, and a taper that facilitates insertion into a tight space. Any or several or all of the features of exemplary closure 420 may be provided by a closure formed in accordance with the principles of the present invention. It will further be appreciated that the closure of the present invention may be applied to packages or cartons other than the day pack of the present invention.

It will be appreciated that various features of above-described day packs 102 and 202, such as, without limitation, a flap that folds away from an inner box, an inner box with a cutaway to facilitate removal of articles therefrom, a closure with its engaging element hidden from view and/or inadvertent access, a closure with a locking tab, and a closure with a feedback feature, may be applied to packages of various shapes and/or sizes, such features not necessarily being limited to packages for tampons or even packages with tapered ends. Various principles of the package of the present invention need not be limited to packaging specifically designed for tampons. Likewise, a package with a tapered end may be beneficial for holding articles other than tampons, and a closure maintaining a tapered end of a package may be applied to any type of package.

It will further be appreciated that the various characteristics of the present invention described above need not be implemented by using all of the above-described inventive features. The various above-described features need not be used in conjunction with each other and are independently beneficial and thus may be used independently or in any combination thereof. For instance, provision of a day pack sized to hold no more than four or five, and preferably four, tampons independently results in a small package of tampons without the further need to align the four or five tampons in a single row. Thus, the shape and configuration of a day pack formed in accordance with the principles of the present invention to contain only a single row of tampons is not essential to the basic concept of a prepackaged day's supply of tampons. Likewise, the configuration of a day pack to hold a single row of tampons independently results in a package that is easy to fit into a small space, without the need for the additional feature of a tapered end of the package. Furthermore, the convenience of day pack 102 is independent of the material and shape of day pack 102. Finally, a tampon package that provides feedback to the user confirming proper closure of the package need not have the other package features described herein.

While the foregoing description and drawings represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A tapered package comprising:
a front wall, a back wall spaced apart from said front wall, first and second side walls spaced apart from each other and extending between said front and back walls, and a bottom wall extending between bottom ends of said front wall, said back wall, and said first and second side walls; wherein top ends of said front wall and said back wall are coupled together such that said package has a tapered shape when viewed from a side; and a closure maintaining said front wall and said back wall together to close said package, said closure comprising (a) engaging elements coupling said front wall and said back wall together, and (b) a cover element covering said engaging elements from view, wherein said closure cover element is in the form of a band extending around and encircling said top ends of said front wall and said back wall to hold said top ends of said front wall and said back wall together to close said tapered package.

* * * * *